United States Patent
Chen et al.

(10) Patent No.: US 9,869,654 B2
(45) Date of Patent: Jan. 16, 2018

(54) METHOD OF MEASURING HEMATOCRIT (HCT), AND MEASUREMENT DEVICE USING THE METHOD

(71) Applicant: BROADMASTER BIOTECH CORP, Zhongli (TW)

(72) Inventors: Yi-Lung Chen, Zhongli (TW); Chien-Hung Lai, Zhongli (TW); Po-Hao Lin, Zhongli (TW); Ya-Sian Lin, Zhongli (TW); Yi-Chen Chen, Zhongli (TW); Fang-Yi Jiang, Zhongli (TW); Shu-Wei Yang, Zhongli (TW); Yu-Hsuan Tai, Zhongli (TW); Shih-Jen Lu, Zhongli (TW)

(73) Assignee: Broadmaster Biotech Corp., Zhongli, Taoyuan County (TW)

( * ) Notice: Subject to any disclaimer, the term of this patent is extended or adjusted under 35 U.S.C. 154(b) by 955 days.

(21) Appl. No.: 14/093,262

(22) Filed: Nov. 29, 2013

(65) Prior Publication Data
US 2015/0153298 A1 Jun. 4, 2015

(51) Int. Cl.
*G01N 27/28* (2006.01)
*G01N 33/48* (2006.01)
*G01N 27/327* (2006.01)
*A61B 5/145* (2006.01)
*G01N 33/49* (2006.01)

(52) U.S. Cl.
CPC ..... *G01N 27/3272* (2013.01); *A61B 5/14535* (2013.01); *G01N 33/49* (2013.01)

(58) Field of Classification Search
CPC ........ G01N 33/49; G01N 33/80; G01N 33/26; G01N 27/327; G01N 27/3272; G01N 27/48; G01N 27/26; G01N 27/3273; A61B 5/14535; A61B 5/05; A61B 5/14532; A61B 5/00; A61B 5/0022; A61B 5/7495

See application file for complete search history.

(56) References Cited

U.S. PATENT DOCUMENTS

| | | | |
|---|---|---|---|
| 8,088,271 B2 | 1/2012 | Fujiwara et al. | |
| 2005/0109637 A1* | 5/2005 | Iyengar | A61B 5/14532 205/775 |
| 2008/0093230 A1* | 4/2008 | Diamond | G01N 27/3274 205/792 |

(Continued)

*Primary Examiner* — Gurpreet Kaur
(74) *Attorney, Agent, or Firm* — Muncy, Geissler, Olds & Lowe, P.C.

(57) ABSTRACT

A method of measuring hematocrit (HCT) and a measurement device using in the method and depends on an electrode test specimen to create a capacitor charging effect and consequential change in discharge current for measurement of hematocrit. The method of measuring hematocrit comprises steps as follows: (a) Instill blood into a pair of test electrodes which is installed in the present invention and apply a voltage to the pair of test electrodes; (b) Remove the voltage applied to the pair of test electrodes and measure a discharge current value; (c) Refer to a predetermined decision rule and the discharge current to obtain a hematocrit value for blood. As such, the present invention which relies on an electrode test specimen in measurement of hematocrit corresponding to a discharge current value during electric discharge contributes to precision and reliability in contrast to conventional hematocrit tests.

5 Claims, 12 Drawing Sheets

(56) References Cited

U.S. PATENT DOCUMENTS

2010/0299072 A1* 11/2010 Kamata .............. G01N 33/5438
　　　　　　　　　　　　　　　　　　　　702/19
2014/0027308 A1* 1/2014 Harrison ............ A61B 5/14532
　　　　　　　　　　　　　　　　　　　　205/777.5

* cited by examiner

HCT61%

| Time(s) | 25mg/dl | 166mg/dl | 311mg/dl | 450mg/dl | 595mg/dl |
|---|---|---|---|---|---|
| 5.00E-03 | 4.29E-04 | 4.89E-04 | 5.31E-04 | 5.63E-04 | 5.98E-04 |
| 1.50E-02 | 3.62E-04 | 4.10E-04 | 4.58E-04 | 5.04E-04 | 5.46E-04 |
| 2.50E-02 | 3.46E-04 | 3.73E-04 | 4.06E-04 | 4.51E-04 | 5.00E-04 |
| 3.50E-02 | 3.38E-04 | 3.58E-04 | 3.78E-04 | 4.10E-04 | 4.57E-04 |
| 4.50E-02 | 3.32E-04 | 3.49E-04 | 3.64E-04 | 3.86E-04 | 4.25E-04 |
| 5.50E-02 | 3.27E-04 | 3.43E-04 | 3.56E-04 | 3.72E-04 | 4.03E-04 |
| 6.50E-02 | 3.23E-04 | 3.38E-04 | 3.49E-04 | 3.62E-04 | 3.88E-04 |
| 7.50E-02 | 3.20E-04 | 3.33E-04 | 3.44E-04 | 3.55E-04 | 3.78E-04 |
| 8.50E-02 | 3.17E-04 | 3.30E-04 | 3.40E-04 | 3.50E-04 | 3.71E-04 |
| 9.50E-02 | 3.14E-04 | 3.26E-04 | 3.36E-04 | 3.45E-04 | 3.65E-04 |
| 0.105 | 3.11E-04 | 3.23E-04 | 3.33E-04 | 3.41E-04 | 3.60E-04 |
| 0.115 | 3.09E-04 | 3.20E-04 | 3.30E-04 | 3.37E-04 | 3.55E-04 |
| 0.125 | 3.07E-04 | 3.18E-04 | 3.27E-04 | 3.34E-04 | 3.51E-04 |
| 0.135 | 3.04E-04 | 3.15E-04 | 3.24E-04 | 3.31E-04 | 3.48E-04 |
| 0.145 | 3.02E-04 | 3.13E-04 | 3.22E-04 | 3.28E-04 | 3.44E-04 |
| 0.155 | 3.01E-04 | 3.11E-04 | 3.19E-04 | 3.25E-04 | 3.41E-04 |
| 0.165 | 2.99E-04 | 3.09E-04 | 3.17E-04 | 3.22E-04 | 3.38E-04 |
| 0.175 | 2.97E-04 | 3.07E-04 | 3.15E-04 | 3.20E-04 | 3.36E-04 |
| 0.185 | 2.96E-04 | 3.05E-04 | 3.13E-04 | 3.18E-04 | 3.33E-04 |
| 0.195 | 2.94E-04 | 3.03E-04 | 3.11E-04 | 3.16E-04 | 3.31E-04 |
| 0.205 | 2.93E-04 | 3.01E-04 | 3.09E-04 | 3.14E-04 | 3.29E-04 |
| 0.215 | 2.91E-04 | 3.00E-04 | 3.08E-04 | 3.12E-04 | 3.26E-04 |
| 0.225 | 2.90E-04 | 2.98E-04 | 3.06E-04 | 3.10E-04 | 3.24E-04 |
| 0.235 | 2.89E-04 | 2.96E-04 | 3.04E-04 | 3.08E-04 | 3.22E-04 |
| 0.245 | 2.87E-04 | 2.95E-04 | 3.03E-04 | 3.06E-04 | 3.20E-04 |
| 0.255 | -1.17E-04 | -1.19E-04 | -1.16E-04 | -1.15E-04 | -1.10E-04 |

FIG. 4

| Time(s) | HCT 0% | HCT 21% | HCT 61% | HCT 72% |
|---|---|---|---|---|
| 5.00E-03 | 5.77E-04 | 5.37E-04 | 4.49E-04 | 4.06E-04 |
| 1.50E-02 | 4.74E-04 | 4.47E-04 | 3.90E-04 | 3.51E-04 |
| 2.50E-02 | 4.41E-04 | 4.22E-04 | 3.75E-04 | 3.35E-04 |
| 3.50E-02 | 4.26E-04 | 4.09E-04 | 3.66E-04 | 3.27E-04 |
| 4.50E-02 | 4.17E-04 | 4.00E-04 | 3.59E-04 | 3.21E-04 |
| 5.50E-02 | 4.09E-04 | 3.93E-04 | 3.54E-04 | 3.16E-04 |
| 6.50E-02 | 4.02E-04 | 3.87E-04 | 3.50E-04 | 3.12E-04 |
| 7.50E-02 | 3.97E-04 | 3.82E-04 | 3.46E-04 | 3.09E-04 |
| 8.50E-02 | 3.91E-04 | 3.77E-04 | 3.42E-04 | 3.06E-04 |
| 9.50E-02 | 3.86E-04 | 3.73E-04 | 3.39E-04 | 3.03E-04 |
| 0.105 | 3.82E-04 | 3.69E-04 | 3.36E-04 | 3.01E-04 |
| 0.115 | 3.78E-04 | 3.66E-04 | 3.33E-04 | 2.99E-04 |
| 0.125 | 3.74E-04 | 3.62E-04 | 3.31E-04 | 2.97E-04 |
| 0.135 | 3.70E-04 | 3.59E-04 | 3.28E-04 | 2.95E-04 |
| 0.145 | 3.67E-04 | 3.56E-04 | 3.26E-04 | 2.93E-04 |
| 0.155 | 3.63E-04 | 3.53E-04 | 3.24E-04 | 2.91E-04 |
| 0.165 | 3.60E-04 | 3.51E-04 | 3.22E-04 | 2.89E-04 |
| 0.175 | 3.57E-04 | 3.48E-04 | 3.20E-04 | 2.87E-04 |
| 0.185 | 3.54E-04 | 3.45E-04 | 3.18E-04 | 2.86E-04 |
| 0.195 | 3.51E-04 | 3.43E-04 | 3.16E-04 | 2.84E-04 |
| 0.205 | 3.48E-04 | 3.41E-04 | 3.15E-04 | 2.83E-04 |
| 0.215 | 3.46E-04 | 3.39E-04 | 3.13E-04 | 2.82E-04 |
| 0.225 | 3.43E-04 | 3.36E-04 | 3.12E-04 | 2.80E-04 |
| 0.235 | 3.41E-04 | 3.34E-04 | 3.10E-04 | 2.79E-04 |
| 0.245 | 3.39E-04 | 3.32E-04 | 3.09E-04 | 2.78E-04 |
| 0.255 | -1.44E-04 | -1.38E-04 | -1.23E-04 | -1.14E-04 |

METHOD OF MEASURING HEMATOCRIT (HCT), AND MEASUREMENT DEVICE USING THE METHOD

BACKGROUND OF THE INVENTION

1. Field of the Invention

The present invention relates to a test method, particularly a method of measuring hematocrit (HCT) and a measurement device using the method.

2. Description of the Related Art

Hematocrit (HCT) is defined as a proportion of red cells in quantitative blood and taken as an indicator to diagnose anemia or cardiovascular diseases in general. Additionally, hematocrit is also a key factor to influence measurement of blood glucose. For a precise blood glucose value, subjects need to measure their hematocrit by which the blood glucose value can be calibrated.

However, it is deficient in conventional measurement of hematocrit manually or in a special tester (e.g., hemacytometer): the manual test is complicated and time-consuming; the special tester is high-priced and needs maintenance cost.

Accordingly, a method or mechanism to promote precision and reliability in measurement of hematocrit deserves to be studied by the persons skilled in the art.

SUMMARY OF THE INVENTION

The present invention is intended to provide a method of measuring hematocrit (HCT) and a measurement device using the method.

The present invention of a method of measuring hematocrit comprises steps as follows: (a) Instill blood into a pair of test electrodes which is installed in the present invention and apply a voltage to the pair of test electrodes; (b) Remove the voltage applied to the pair of test electrodes and measure a discharge current value; (c) Refer to a predetermined decision rule and the discharge current to obtain a hematocrit value for the blood.

The present invention of a measurement device using the method comprises: a test unit which comprises a pair of test electrodes consisting of a receiver part to carry blood and a contact part; a detector which links the contact part in the pair of test electrodes to apply a voltage to the contact part, remove the voltage, and get a hematocrit value by referring to a predetermined decision rule.

The present invention based on an electrode test specimen to measure discharge current and hematocrit contributes to precision and reliability.

BRIEF DESCRIPTION OF THE DRAWINGS

FIG. 4 illustrates data of current versus time for five different glucose concentrations in the present invention (HCT=61%).

FIG. 11 illustrates data of current versus time for HCT=0%, HCT=21%, HCT=61%, and HCT=72%.

DETAILED DESCRIPTION OF THE PREFERRED EMBODIMENTS

Figure 1:
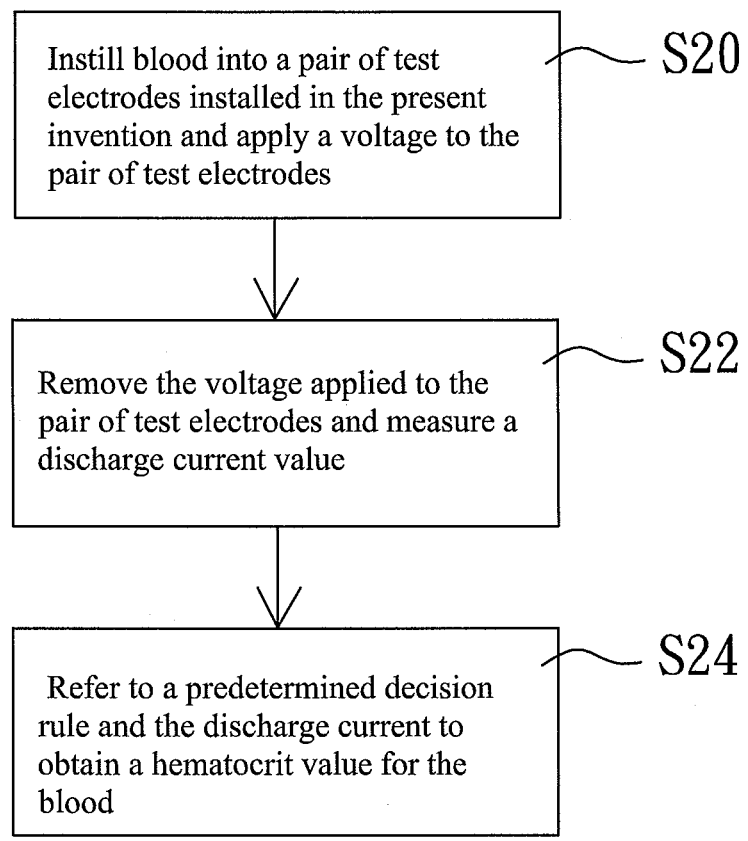
FIG. 1 is a flow diagram illustrating the present invention of a method of measuring hematocrit.

The present invention of a method of measuring hematocrit is presented in the following sections. Refer to FIG. 1 which is a flow diagram that illustrates the present invention of a method of measuring hematocrit and comprising steps as follows:

Step 1: Instill blood into a pair of test electrodes installed in the present invention and apply a voltage to the pair of test electrodes (S20);

Step 2: Remove the voltage applied to the pair of test electrodes and measure a discharge current value (S22); and Step 3: Refer to a predetermined decision rule and the discharge current to obtain a hematocrit value for the blood (S24).

In Step 1, the voltage applied to the pair of test electrodes should be within the range from 1 to 3 volts within 0.01 through 1 second.

In Step 1, the pair of test electrodes separated by a closer distance will create a higher capacitance, for example, a distance between 0.6 mm and 0.05 mm is in a preferable embodiment.

Because the discharge current is higher in Step 2 in the beginning of electro-discharge then the latter, so it has better resolution contributing to measurement, just removed, for example, less than 0.005 second after start of electric discharge, has better resolution contributing to measurement.

In Step 3, the predetermined decision rule for hematocrit refers to multiple data which present relationships between hematocrit and discharge current values corresponding to different voltage values.

Figure 2:
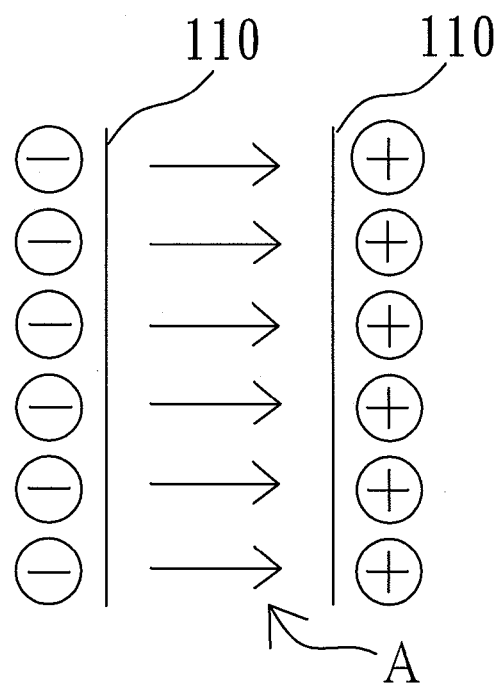
FIG. 2 is a schematic view which illustrates a voltage applied by the present invention.

The factors influencing precision of the present invention of a method of measuring hematocrit are disclosed as follows. Refer to FIG. 2 which illustrates response current measured with a voltage applied and FIG. 3 which illustrates discharge current measured with a voltage removed. As shown in FIG. 2, the pair of test electrodes 110 to which a voltage is applied for capacitor charging generates response current with a direction and status indicated in A. In the case of HCT fixed, the response current values, which are affected by some factors such as redox reaction, glucose concentration, cholesterol and urea, will be different from each other. Furthermore, hematocrit will be less precise when it depends on a measured response current as well as a decision rule for relationships between hematocrit and response currents corresponding to different voltages.

Figure 3:
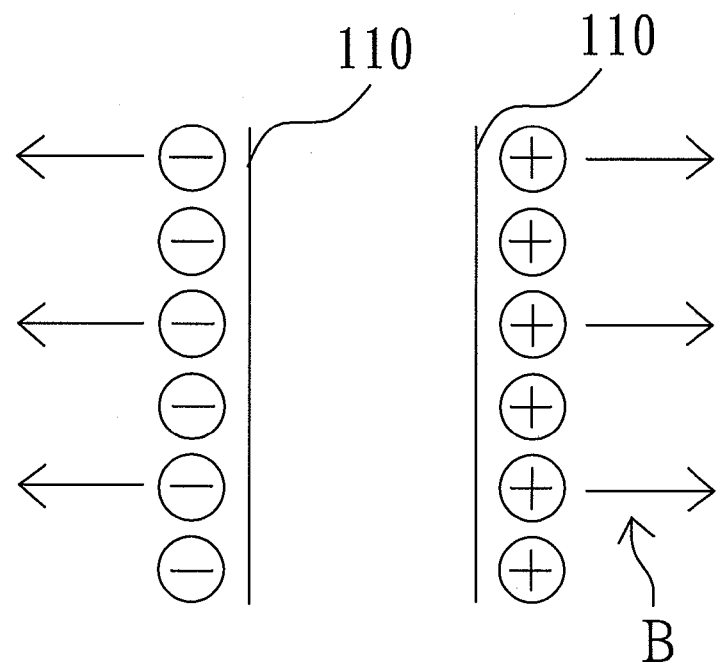
FIG. 3 is a schematic view which illustrates a voltage applied is removed in the present invention.
Figure 5:
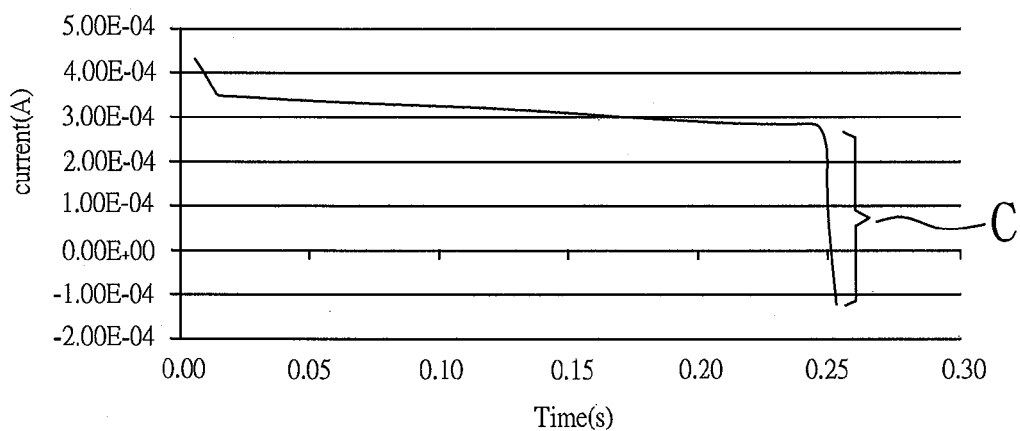
FIG. 5 is a graph of current versus time for the glucose concentration of 25 mg/dl in the present invention.
Figure 6:
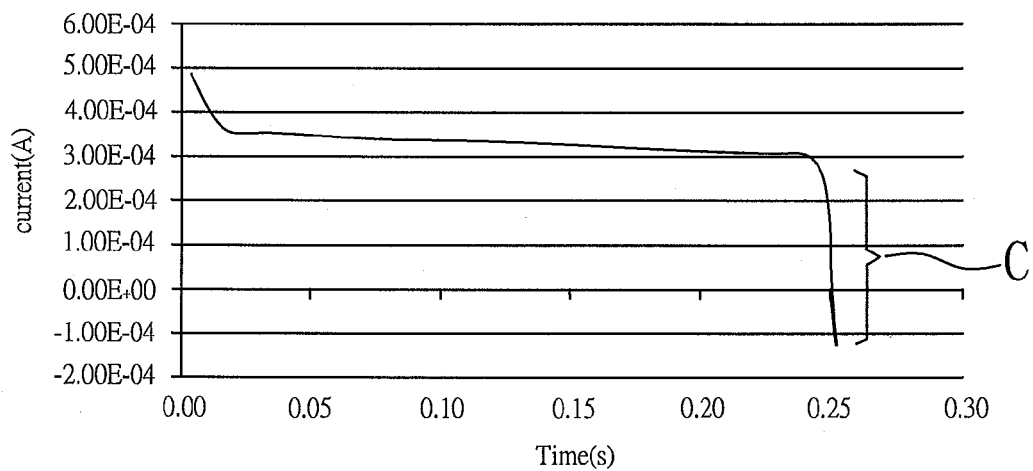
FIG. 6 is a graph of current versus time for the glucose concentration of 166 mg/dl in the present invention.
Figure 7:
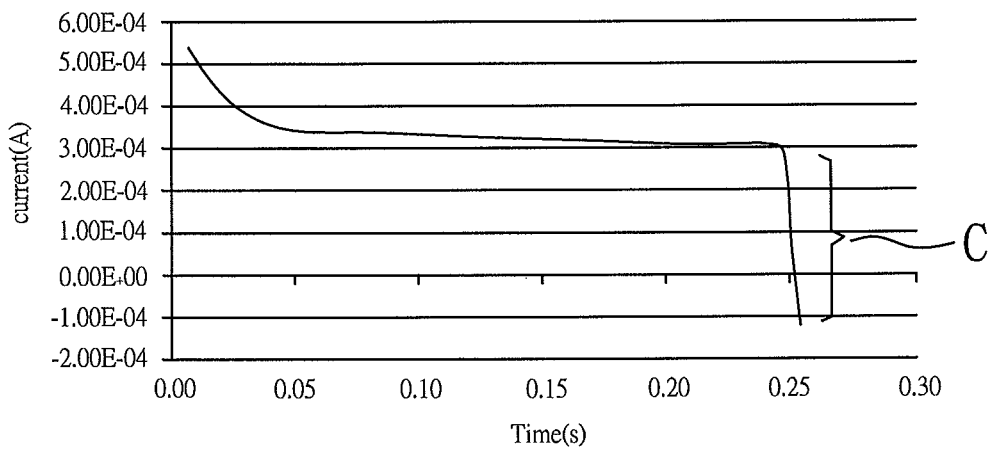
FIG. 7 is a graph of current versus time for the glucose concentration of 311 mg/dl in the present invention.
Figure 8:
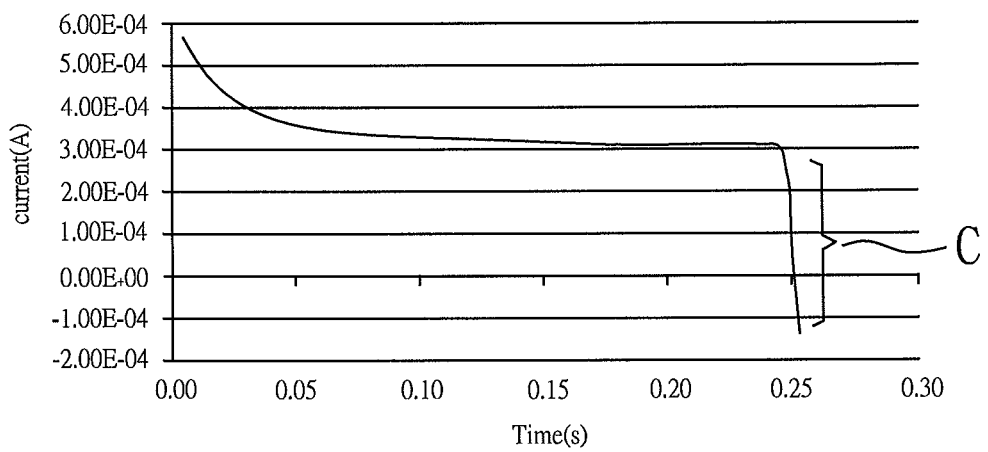
FIG. 8 is a graph of current versus time for the glucose concentration of 450 mg/dl in the present invention.
Figure 9:
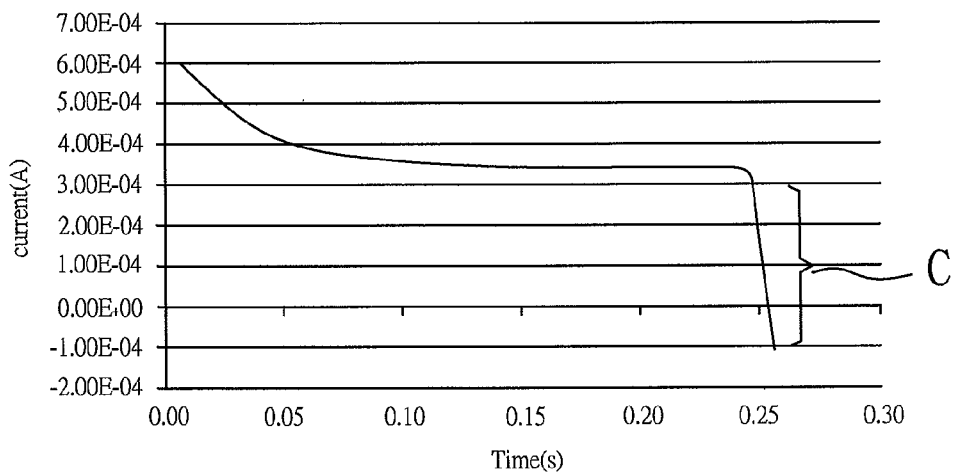
FIG. 9 is a graph of current versus time for the glucose concentration of 595 mg/dl in the present invention.

With a voltage applied for one period and removed later, the pair of test electrodes 110 in FIG. 3 starts a discharge process in which discharge current with a direction and status indicated in B is not affected by a redox reaction but by hematocrit. Accordingly, a measured hematocrit value based on a predetermined decision rule and the discharge current in Step 3 of the present invention is more precise.

Figure 10:
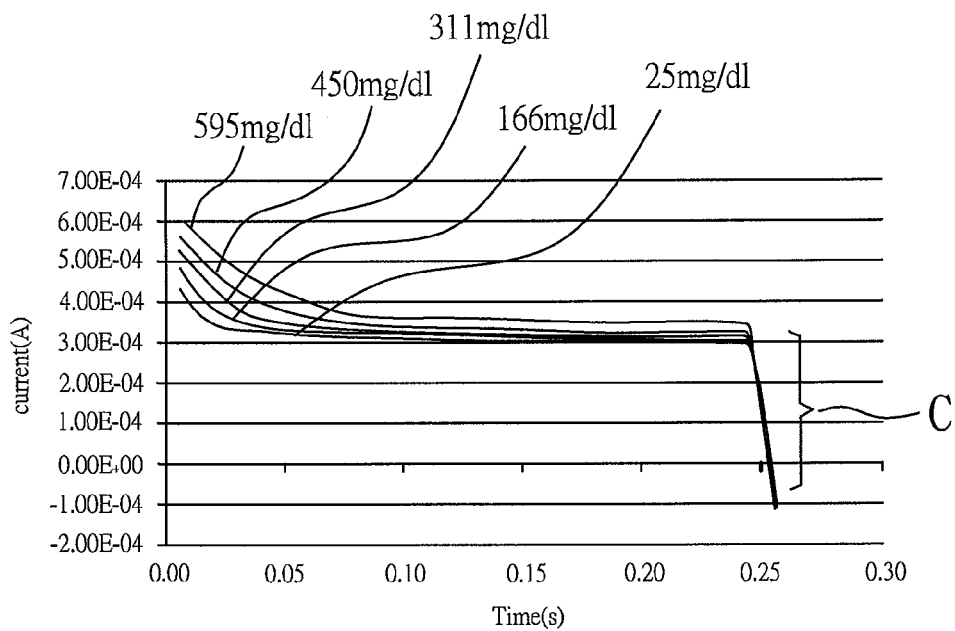
FIG. 10 is a graph for data of current versus time summarized from FIG. 5 to FIG. 9.

It can be seen from experimental data that the present invention of a method of measuring hematocrit is not affected by glucose concentrations. Refer to FIG. 4 through FIG. 10: FIG. 5 through FIG. 9 are plots of current versus time based on data in FIG. 4 for glucose concentrations of 25 mg/dl, 166 mg/dl, 311 mg/dl, 450 mg/dl and 595 mg/dl sequentially; FIG. 10 illustrates data of current versus time summarized from FIG. 5 to FIG. 9. FIG. 4 illustrates experimental data of current (unit: amp) versus time (unit: second) for five different glucose concentrations at HCT=61%. In these figures, any point-in-time at which a current value is abruptly decreased is the moment that a voltage is removed.

As shown in FIG. 5 through FIG. 9, discharge current measured at area C in which a specific voltage is applied first and removed later is not affected by glucose concentrations, cholesterol and urea and contributes to precision of hematocrit. As shown in FIG. 10, the discharge current values at area C measured in samples for five different glucose concentrations and HCT=61% are almost equal and contribute to precision of hematocrit. However, the response current values measured in samples with five different glucose concentrations during application of a specific voltage to the pair of test electrodes constantly are different from each other and result in hematocrit values less precise.

The present invention of a method of measuring hematocrit is further described with experimental data as follows. Refer to FIG. 11 through FIG. 15. FIG. 11 illustrates experimental data of current (unit: amp) versus time (unit: second) for HCT=0%, HCT=21%, HCT=61%, and HCT=72%. FIG. 12 through FIG. 15 are plots of current versus time based on data in FIG. 11 for HCT=0%, HCT=21%, HCT=61%, and HCT=72%; any point-in-time at which a current value is abruptly decreased is the moment that a voltage is removed.

Figure 12:
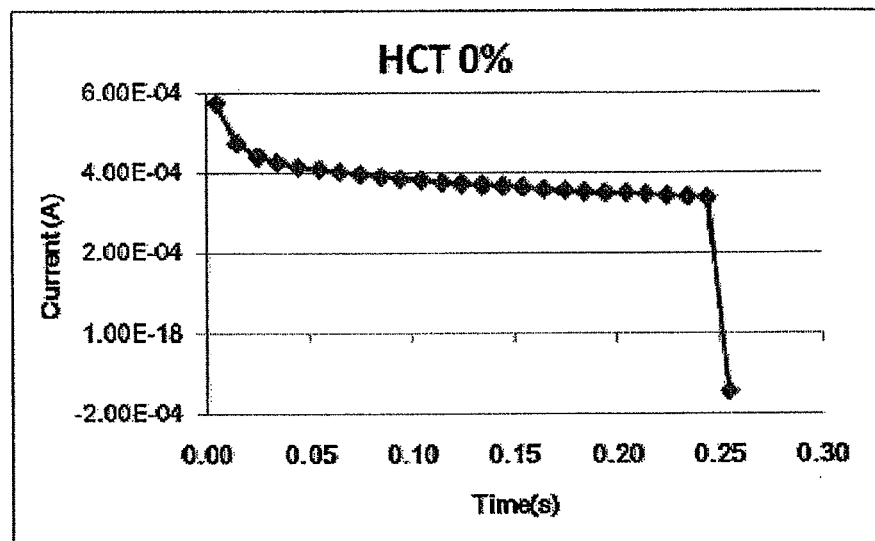
FIG. 12 is a graph of current versus time based on data in FIG. 11 for HCT=0%.
Figure 13:
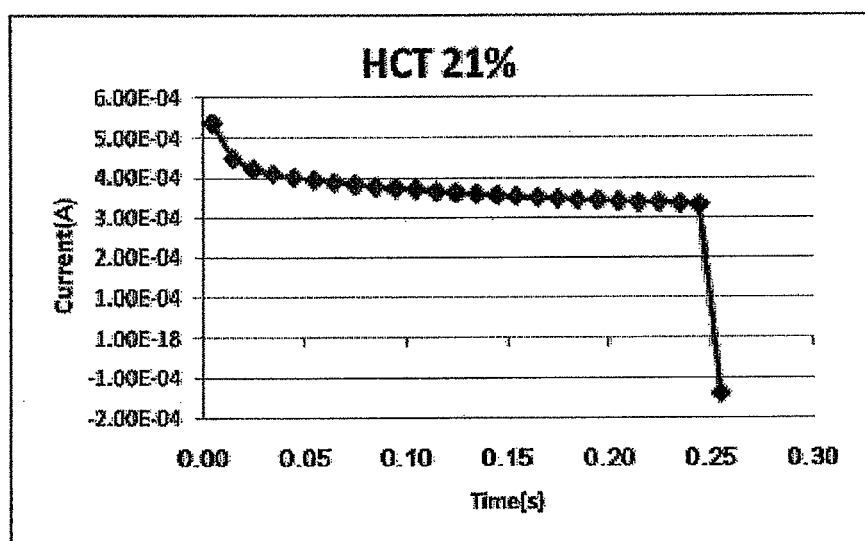
FIG. 13 is a graph of current versus time based on data in FIG. 11 for HCT=21%.
Figure 14:
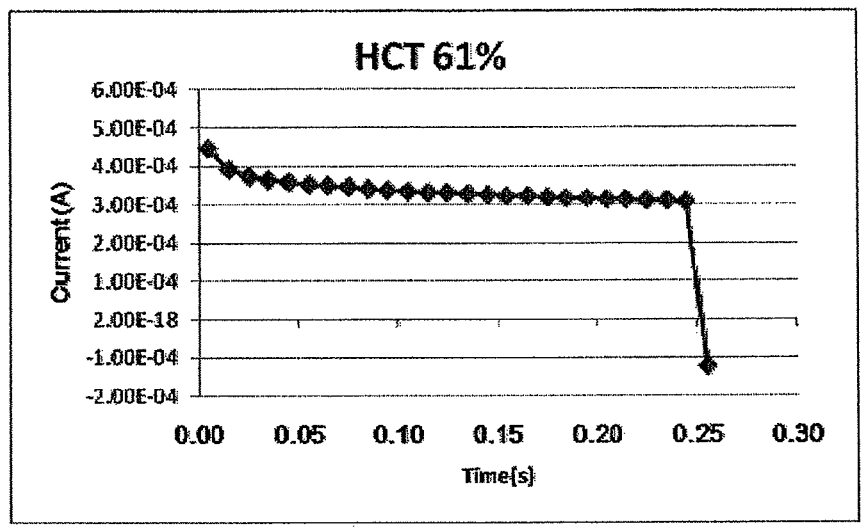
FIG. 14 is a graph of current versus time based on data in FIG. 11 for HCT=61%.
Figure 15:
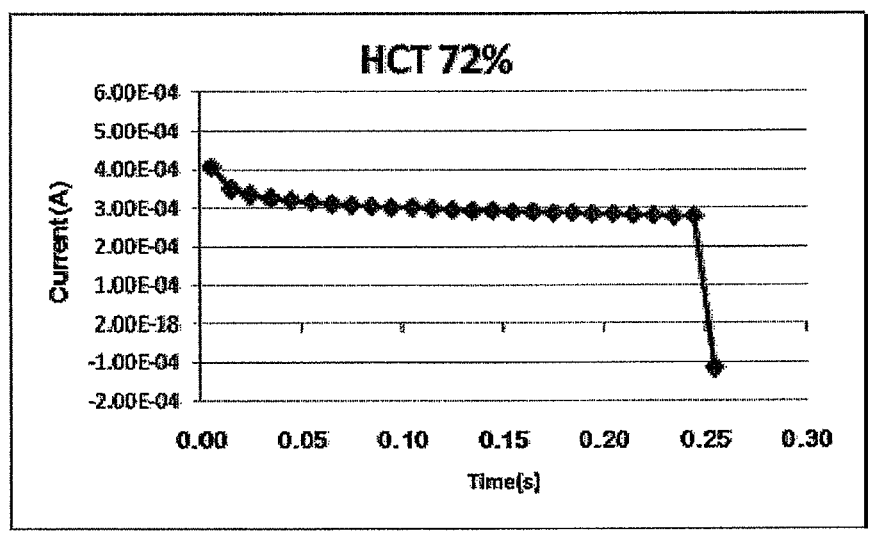
FIG. 15 is a graph of current versus time based on data in FIG. 11 for HCT=72%.

FIGS. 11 and 12 illustrate a discharge current value measured at T=0.255 second and HCT=0% is −1.44E-04 amp after an applied voltage is removed at T=0.25 second; FIGS. 11 and 13 illustrate a discharge current value measured at T=0.255 second and HCT=21% is −1.38E-04 amp after an applied voltage is removed at T=0.25 second; FIGS. 11 and 14 illustrate a discharge current value measured at T=0.255 second and HCT=61% is −1.23E-04 amp after an applied voltage is removed at T=0.25 second; FIGS. 11 and 15 illustrate a discharge current value measured at T=0.255 second and HCT=72% is −1.14E-04 amp after an applied voltage is removed at T=0.25 second. From the foregoing, the present invention of a method of measuring hematocrit contributes to a precise hematocrit value because discharge current values corresponding to multiple hematocrit values are different.

Figure 16:
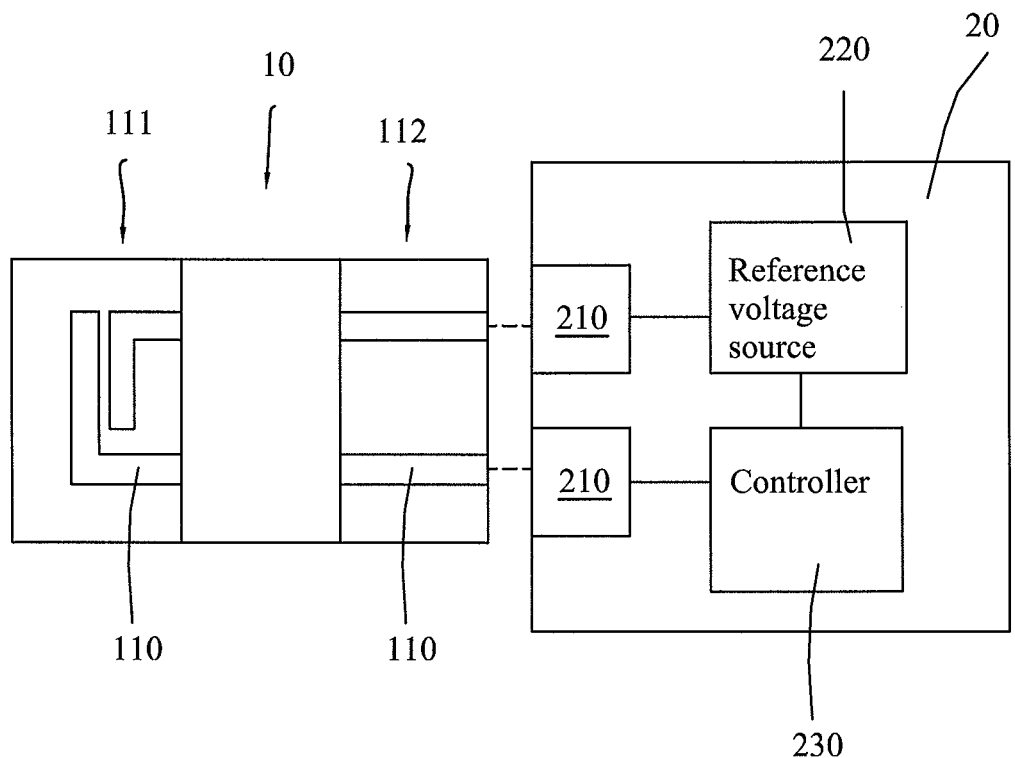
FIG. 16 is a schematic view which illustrates the present invention of a measurement device is using the method of measuring hematocrit in one embodiment.

A measurement device using the present invention of a method of measuring hematocrit is described in embodiments as follows. Refer to FIG. 16 which is a schematic view that illustrates the present invention of a measurement device using the method of measuring hematocrit in one embodiment. The measurement device for hematocrit comprises a test unit 10 and a detector 20. The test unit 10 comprises a pair of test electrodes 110 which consists of a receiver part 111 to carry blood and a contact part 112. The detector 20 which is connected to the contact part 112 in the pair of test electrodes 110 applies a voltage to the contact part 112, removes the voltage, and gets hematocrit by referring to a predetermined decision rule.

The detector 20 comprises a pair of ports 210, a reference voltage source 220 and a controller 230: each of the ports 210 has a first end to link the contact part 112; the reference voltage source 220 links a second end in one of the ports 210 to supply a voltage for tests; the controller 230 links a second end in the other of the ports 210 and the reference voltage source 220 to receive a discharge current value out of the test unit 10 and get hematocrit with a voltage from the reference voltage source 220 applied for one period and removed later.

Figure 17:
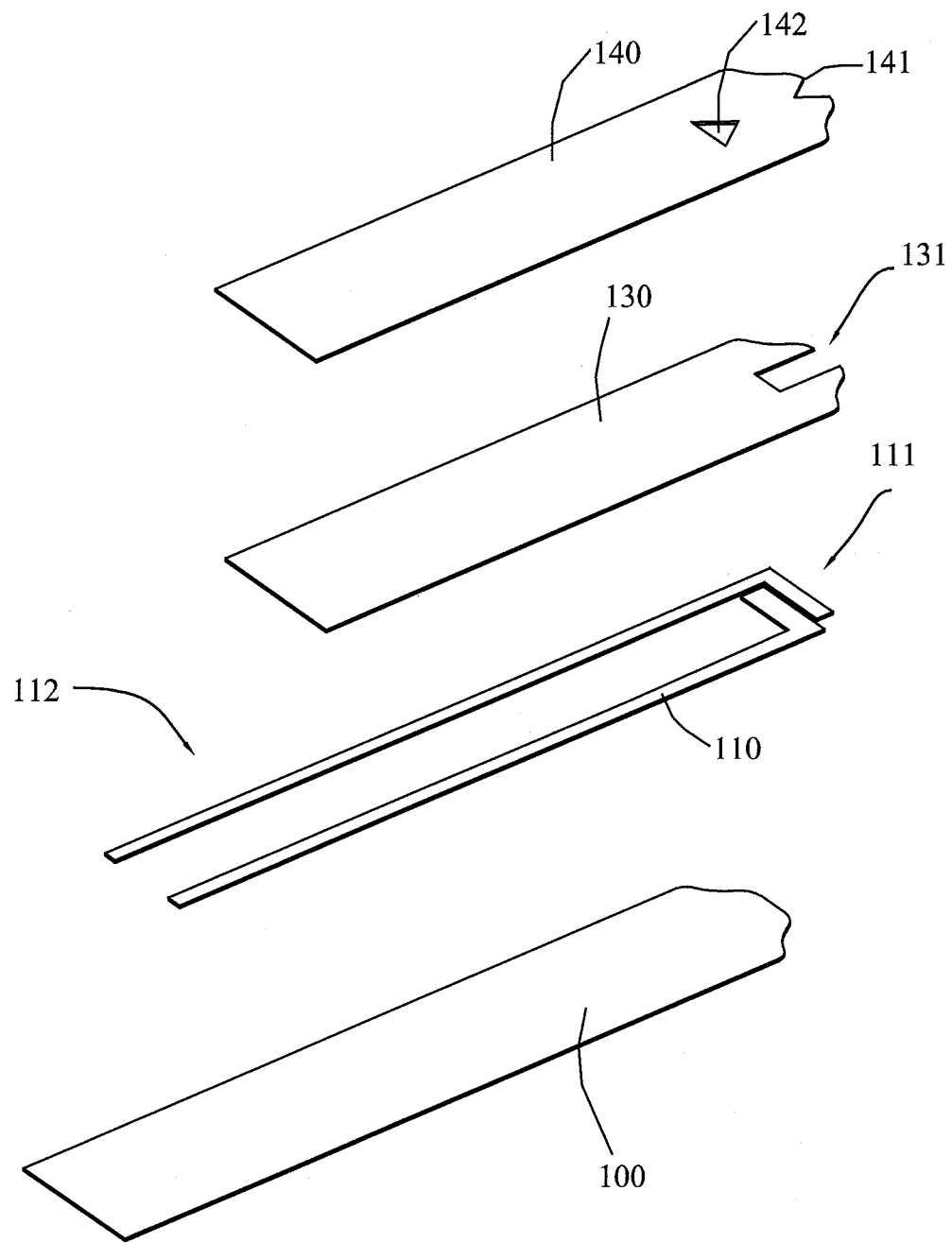
FIG. 17 is an exploded view illustrating a test unit in the present invention of a measurement device for hematocrit in one embodiment.
Figure 18:
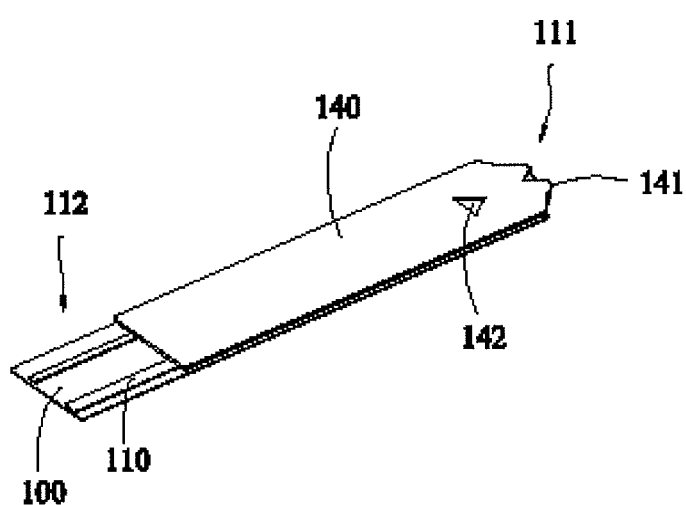
FIG. 18 is a schematic view illustrating a test unit in the present invention of a measurement device for hematocrit in one embodiment.

FIG. 17 is an exploded view illustrating a test unit in the present invention of a measurement device for hematocrit in one embodiment; FIG. 18 is a schematic view illustrating a test unit in the present invention of a measurement device for hematocrit in one embodiment. As shown in FIG. 17 for one embodiment, the test unit 10 which is designed as a test specimen comprises a substrate 100, the pair of test electrodes 110, a baffle 130 and a cover sheet 140: the pair of test electrodes 110 is mounted on the substrate 100; the baffle 130 mounted on the substrate 100 has some parts over the pair of test electrodes 110 for the electrodes' rear ends exposed and develops an opening 131 which is designed at one front end of the baffle 130 and makes the electrodes' corresponding front parts exposed.

As mentioned, the receiver part 111 in the pair of test electrodes 110 is defined as a region exposed to the opening 131; the contact part 112 is defined as rear electrodes of the pair of test electrodes 110 not covered by the baffle 130.

The cover sheet 140 over the baffle 130 develops a notch 141 and a pilot hole 142: the notch 141 is designed at one front end of the cover sheet 140, overlapping the opening 131 of the baffle 130; the pilot hole 142 opened on the cover sheet 140 corresponds to the opening 131 on the baffle 130 for development of a conduction route.

When blood collected in a dedicated blood lancet is instilled into the notch 141, the conduction route from the notch 141 to the opening 131 of the baffle 130 will create capillarity by which blood is introduced to the test unit 10 through the opening 131 and contacts the pair of test electrodes 110. Then, the detector 20 is activated with the contact part 112 on the pair of test electrodes 110 linking the pair of ports 210 on the detector 20.

The controller 230 drives the reference voltage source 220 to apply a voltage between the pair of test electrodes 110 for creations of an electrochemical reaction in blood and a conduction route of response current. After the applied voltage is removed, a discharge current value depending on hematocrit is changed and read by the controller 230 for determination of hematocrit about the blood. The controller 230 is able to identify hematocrit in a fixed time interval by referring to different discharge current values.

In order to effectively and precisely read discharge current values for conversion into hematocrit, the controller 230 should be setup beforehand (for example with an electrochemical meter), data of discharge current values versus hematocrit in percentage is saved in the controller 230 for the conversion of measured discharge current values.

Accordingly, the present invention which relies on an electrode test specimen in measurement of hematocrit corresponding to a discharge current value during electric discharge contributes to precision and reliability in contrast to conventional hematocrit tests.

The above descriptions for the present invention are preferred embodiments which do not limit the scope of the present invention; any change or promotion made by any person skilled in the art is referred to as a purpose not departing from the spirit of the present invention.

What is claimed is:

1. A method of measuring hematocrit, comprising:
   Step 1: Instill blood into a pair of test electrodes and apply a voltage to said pair of test electrodes;
   Step 2: Remove said voltage applied to said pair of test electrodes and measure a discharge current value; and
   Step 3: Refer to a predetermined decision rule and said discharge current value to obtain a hematocrit value for blood,
   wherein said measuring a discharge current value in Step 2 is to measure a discharge current value in less than 0.005 second after said voltage is removed.

2. The method of measuring hematocrit according to claim 1 characterized in that said applied voltage to said pair of test electrodes in Step 1, said applied voltage is between 1 and 3 volts.

3. The method of measuring hematocrit according to claim 1 characterized in that said applied voltage to said pair of test electrodes in Step 1, a duration of said applied voltage is within 0.01 through 1 second.

4. The method of measuring hematocrit according to claim 1 characterized in that said pair of test electrodes in Step 1 is separated by a distance of 0.6 mm to 0.05 mm.

5. The method of measuring hematocrit according to claim 1 characterized in that said predetermined decision rule in Step 3 comprises multiple hematocrit data which presents relationships between hematocrit and discharge current values under different voltage values for determining a hematocrit value of said blood.

* * * * *